United States Patent
Won et al.

(10) Patent No.: US 12,180,300 B2
(45) Date of Patent: Dec. 31, 2024

(54) TARGETING MOIETY-DRUG GRAFTED IMMUNE CELL COMPOSITIONS AND METHODS OF USE

(71) Applicants: ARIZONA BOARD OF REGENTS ON BEHALF OF THE UNIVERSITY OF ARIZONA, Tucson, AZ (US); UNIVERSITY OF UTAH RESEARCH FOUNDATION, Salt Lake City, UT (US)

(72) Inventors: Youngwook Won, Tucson, AZ (US); David A. Bull, Tucson, AZ (US); Daniel Yongwon Lee, Tucson, AZ (US)

(73) Assignees: ARIZONA BOARD OF REGENTS ON BEHALF OF THE UNIVERSITY OF ARIZONA, Tucson, AZ (US); UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 957 days.

(21) Appl. No.: 17/277,828

(22) PCT Filed: Sep. 20, 2019

(86) PCT No.: PCT/US2019/052097
§ 371 (c)(1),
(2) Date: Mar. 19, 2021

(87) PCT Pub. No.: WO2020/061419
PCT Pub. Date: Mar. 26, 2020

(65) Prior Publication Data
US 2021/0353768 A1 Nov. 18, 2021

Related U.S. Application Data

(60) Provisional application No. 62/733,929, filed on Sep. 20, 2018.

(51) Int. Cl.
| | | |
|---|---|---|
| C07K 16/32 | (2006.01) | |
| A61K 47/60 | (2017.01) | |
| A61K 47/68 | (2017.01) | |
| A61K 47/69 | (2017.01) | |
| A61P 35/00 | (2006.01) | |

(52) U.S. Cl.
CPC .............. *C07K 16/32* (2013.01); *A61K 47/60* (2017.08); *A61K 47/68033* (2023.08); *A61K 47/6849* (2017.08); *A61K 47/6855* (2017.08); *A61K 47/6901* (2017.08); *A61P 35/00* (2018.01)

(58) Field of Classification Search
CPC ................ A61K 47/6901; A61K 47/60; A61K 47/6803; A61K 47/6849; A61K 47/6855; A61K 47/6851; A61P 35/00; C07K 2317/24; C07K 2317/77; C07K 16/32; C12N 5/0646; C12N 2510/00

See application file for complete search history.

(56) References Cited

U.S. PATENT DOCUMENTS

| | | | |
|---|---|---|---|
| 2016/0120807 A1 | 5/2016 | Maldonado et al. | |
| 2016/0130358 A1 | 5/2016 | Bhakta et al. | |
| 2016/0361360 A1 | 12/2016 | Chang et al. | |
| 2017/0000894 A1* | 1/2017 | Won | A61K 35/28 |
| 2017/0112800 A1 | 5/2017 | Roy et al. | |
| 2018/0200196 A1 | 7/2018 | Fahmy et al. | |

FOREIGN PATENT DOCUMENTS

| | | |
|---|---|---|
| CN | 107789366 A | 3/2018 |
| WO | 2005021730 A2 | 3/2005 |
| WO | 2010126319 A2 | 11/2010 |
| WO | 2016167809 A1 | 10/2016 |
| WO | 2018005973 A1 | 1/2018 |

OTHER PUBLICATIONS

Zhao Y et al. A Herceptin-Based Chimeric Antigen Receptor with Modified Signaling Domains Leads to Enhanced Survival of Transduced T Lymphocytes and Antitumor Activity (J Immunol (2009) 183 (9): 5563-5574) (Year: 2009).*
Diessner J et al. Targeting of preexisting and induced breast cancer stem cells with trastuzumab and trastuzumab emtansine (T-DM1) (Cell Death Dis. Mar. 2014; 5(3): e1149 1-13). (Year: 2014).*
Wang Y et al. Activating Autophagy Enhanced the Antitumor Effect of Antibody Drug Conjugates Rituximab-Monomethyl Auristatin E (Front Immunol. 2018; 9: 1799 1-12) (Year: 2018).*
Dall'Ozzo S et al. Rituximab-Dependent Cytotoxicity by Natural Killer Cells: Influence of FCGR3A Polymorphism on the Concentration-Effect Relationship (Cancer Res (2004) 64 (13): 4664-4669). (Year: 2004).*
International Preliminary Report on Patentability for Application No. PCT/US2019/052097 dated Mar. 23, 2021 (8 pages).
International Search Report and Written Opinion for Application No. PCT/US2019/052097 dated Dec. 4, 2019 (10 pages).
Barok, M. et al. "Trastuzumab emtansine: mechanisms of action and drug resistance." Breast cancer research 16.2 (2014): 1-12.
European Patent Office Extended European Search Report for application 19863403.2, dated Oct. 19, 2022 (11 pages).

(Continued)

*Primary Examiner* — Karen A. Canella
*Assistant Examiner* — John J Skoko, III
(74) *Attorney, Agent, or Firm* — Michael Best & Friedrich LLP

(57) ABSTRACT

Surface-engineered immune cells, such as natural killer cells, grafted with targeting moiety-drug complexes. The present invention combines chemotherapy and immunotherapy by engineering the immune cells to target specific tumor cells through antigen recognition and deliver potent chemotherapeutic agents, thereby destroying the tumor cells. The surface-engineered immune cells may be prepared using a one-step method. The present invention also provides kits for preparing the surface-engineered immune cells.

8 Claims, 8 Drawing Sheets

(56) References Cited

OTHER PUBLICATIONS

Shao, S., et al. "Site-specific and hydrophilic ADCs through disulfide-bridged linker and branched PEG." Bioorganic & Medicinal Chemistry Letters 28.8 (2018): 1363-1370.
Japanese Patent Office Notice of Reason for Rejection for application 2021-516606, dated Sep. 128, 2023 (11 pages with translation).
Won, Y.-W. et al. "Cell surface engineering to enhance mesenchymal stem cell migration toward an SDF-1 gradient." Biomaterials 35.21 (2014): 5627-5635.
Xiao, H., et al. "Precision glycocalyx editing as a strategy for cancer immunotherapy." Proceedings of the National Academy of Sciences 113.37 (2016): 10304-10309.
Yamamoto, T., et al. "Interaction of poly (ethylene glycol)-conjugated phospholipids with supported lipid membranes and their influence on protein adsorption." Science and Technology of advanced MaTerialS 17.1 (2016): 677-684.
Yonezawa, A., et al. "Boosting cancer immunotherapy with anti-CD137 antibody therapy." Clinical Cancer Research 21.14 (2015): 3113-3120.
Nag, O. L. et al. "Surface engineering of liposomes for stealth behavior." Pharmaceutics 5.4 (2013): 542-569.
Korean Patent Office Office Action for application 10-2021-7011380, dated Oct. 20, 2024 (20 pages with machine translation).

\* cited by examiner

TARGETING MOIETY-DRUG GRAFTED IMMUNE CELL COMPOSITIONS AND METHODS OF USE

CROSS-REFERENCE TO RELATED APPLICATION(S)

This is a U.S. national stage entry of International Patent Application No. PCT/US2019/052097, filed on Sep. 20, 2019, which claims priority to U.S. Provisional Patent Application No. 62/733,929, filed on Sep. 20, 2018, the entire contents of each of which are fully incorporated herein by reference.

BACKGROUND OF THE INVENTION

The present invention relates to cancer therapies that target specific cancer cells, more particularly to methods and compositions that combine chemotherapy and immunotherapy, such as compositions comprising targeting moiety-drug complexes or targeting moiety-drug grafted immune cells (surface engineered immune cells) for targeting and destroying specific cancer cells. The present invention also relates to methods for preparing the targeting moiety-drug grafted immune cells (surface engineered immune cells) by embedding targeting moiety-drug complexes on and/or in the immune cell membrane, as well as methods of use of the targeting moiety-drug grafted immune cells (surface engineered immune cells).

Effective chemoimmunotherapy is thought to require that chemotherapeutic agents induce cancer cell death and promote immunomodulation, targeted chemotherapy minimizes the adverse effects on immune cells, and immune effector cells maintain their cytolytic activity against cancer cells.

The present invention features methods and compositions for combining chemotherapy and immunotherapy for the development of targeted cancer chemoimmunotherapy. In this combinatorial approach, targeting moiety-drug complexes (e.g., antibody-drug conjugates (ADCs)) are introduced to the surface of immune cells. The process of embedding targeting moiety-drug complexes (e.g., ADCs) on and/or in the immune cell surface may exploit the hydrophobic interaction between a polymeric lipid chain and the lipid bilayer of the cell membrane. Lipid-conjugated targeting moiety-drug complexes (e.g., hydrophobized targeting moiety-drug complexes) may be incorporated into the lipid bilayer without disrupting the cell membrane integrity and award new functions to the surface-engineered cells. Inventors have surprisingly found that the surface-engineered immune cells herein, e.g., the immune cells featuring targeting moiety-drug complexes (e.g., ADCs) as described herein, can simultaneously deliver potent chemotherapeutic agents to a target tumor and enhance the homing of adoptively transferred immune cells toward the tumor sites without compromising their cytotoxic activities. This may ultimately intensify the combinatorial anticancer efficacy to combat cancer.

While the attachment of targeting proteins or peptides has been attempted on stem cells, the goal of the technology was to recruit cells to a particular area for regeneration purposes. In the present invention, however, targeting moiety-drug complexes are attached to immune cells, such as natural killer (NK) cells, for the purposes of killing cells, such as cancer cells. Further, the entities that are used to target and deliver cells to a target cell are different. For example, in certain embodiments, the present invention uses cancer cell markers for targeting purposes.

BRIEF SUMMARY OF THE INVENTION

The present invention features compositions that combine chemotherapy and immunotherapy for the development of targeted cancer chemoimmunotherapy. The compositions herein comprise a targeting moiety-drug complex, which is attached to an immune cell via a phospholipid-polyethylene glycol (PEG) linker. For example, the targeting moiety-drug complex may be incorporated into the lipid bilayer of the immune cell via the phospholipid-PEG linker. Without wishing to limit the present invention to any theory or mechanism, it is believed that the surface engineered immune cells of the present invention (e.g., the targeting moiety-drug complex incorporated on and/or in the surface of the immune cell) can (1) enhance homing of the modified (surface engineered) immune cells toward the target cells, e.g., cancer cells, and thus increase the density of immune cells in the environment, e.g., tumor environment; and (2) block tumor growth and/or kill cancer cells. These two events may trigger cancer cell death synergistically and activate the immune system, the latter of which can kill metastatic cancer cells and/or circulating tumor cells. The present invention is not limited to the targeting moiety-drug complexes (or ADCs) described herein, such as those featuring T-DM1. Any appropriate antibody-drug conjugates or targeting moiety-drug complexes, including those currently marketed and undergoing development, can be incorporated on the surface of an immune cell (e.g., any immune cell) using the methods and compositions described herein.

Briefly, the present invention features chemoimmunotherapeutic compositions for targeting a cells, e.g., cancer cells. In certain embodiment, the composition comprises a targeting moiety specific for and capable of binding to a target on a cell of interest; a drug conjugated on the targeting moiety forming a targeting moiety-drug complex; a phospholipid linked to a polyethylene glycol (PEG) forming a phospholipid-PEG linker, wherein the phospholipid-PEG linker is attached to the targeting moiety-drug complex; and an immune cell, wherein the targeting moiety-drug complex is hydrophobically bound to the immune cell via the phospholipid-PEG linker. In certain embodiments, the targeting moiety-drug complex directs the immune cell to the cell of interest, wherein the drug has a cytotoxic effect on the cell of interest.

In certain embodiments, the phospholipid is selected from the group consisting of 1,2-dimyristoyl-sn-glycero-3-phosphoethanolamine, 1,2-dipalmitoyl-sn-glycero-3-phosphoethanolamine and 1,2-distearoyl-sn-glycero-3-phosphocholine. In some embodiments, the PEG has a molecular weight from 2 kDa to 10 kDa. In some embodiments, the PEG has a molecular weight from 4.5 kDa to 5.5 kDa. In some embodiments, the cell of interest is a breast cancer cell. In some embodiments, the immune cell is selected from the group consisting of: a natural killer (NK) cell, a lymphocyte, a leukocyte, and a phagocyte. In some embodiments, the immune cell is a combination of two or more cells from the group consisting of; a natural killer (NK) cell, a lymphocyte, a leukocyte, and a phagocyte. In some embodiments, the lymphocyte is a natural killer (NK) cell. In some embodiments, the target is HER2. In some embodiments, the targeting moiety is an antibody or fragment thereof. In some embodiments, the targeting moiety is an anti-HER2 antibody. In some embodiments, the targeting moiety is trastuzumab, alemtuzumab, pertuzumab, bevacizumab, or rituximab. In some embodiments, the targeting moiety is an anti-CD53 antibody, an anti-CD30 antibody, an anti-CD20 antibody, an anti-Ep-CAM antibody, an anti-VEGF antibody, an anti-VEGFR antibody, an anti-MSLN antibody, an anti-CD319 antibody, an anti-phosphatidylserine antibody, an anti-FGFR antibody, an anti-CD44 antibody, an anti-Notch1 antibody, an anti-mucin antibody, an anti-MCP-1 antibody, an anti-Lewis-Y antigen antibody, an anti-PCDC1 antibody, an anti-IL2 antibody, an anti-EGFR antibody, an anti-CEACAM5 antibody, an anti-MUC1 antibody, an anti-glypican 3 antibody, an anti-PTK7 antibody, an anti-CD19 antibody, an anti-RANKL antibody, an anti-B lymphoma cell antibody, an anti-DR5 antibody, an anti-CLDN19 antibody, an anti-HERS antibody, an anti-HER1 antibody, an anti-CD4 antibody, or an anti-CD70 antibody. In some embodiments, the drug is emtansine (DM1).

The present invention also features methods for treating a tumor in a subject in need thereof. In certain embodiments, the method comprises administering to the subject a therapeutically effective amount of composition according to the present invention, wherein the targeting moiety is specific for a target on cells of the tumor. In certain embodiments, the drug has a cytotoxic effect on cells of the tumor.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 1A shows a comparison of cell viabilities between unmodified NK cells and SE-NK/T-DM1 cells generated with 50, 100, or 200 μg of DMPE-PEG-T-DM1. Data=mean±SD.

FIG. 1B shows the surface retention time of T-DM1 on the surface of SE-NK/T-DM1 cells incubated in media containing 10% serum. SE-NK/T-DM1 cells were incubated in complete growth media and a portion of cells were sampled at each time point up to 48 h. The presence of T-DM1 on the surface of SE-NK/T-DM1 cells was detected using Alexa 488-conjugated goat anti-human IgG (H+L) antibodies, Plot is selected from two independent experiments.

FIG. 1C shows the availability of CD56 and 2B4 on the cell membrane of SE-NK/T-DM1-FITC cells was determined by flow cytometry. After SE-NK/T-DM1-FITC cells were prepared, APC-conjugated anti-CD56 antibodies or APC-conjugated anti-2B4 antibodies were used to detect the receptor availability. All images and plots are from one of two independent experiments, FIG. 2 shows binding of SE-NK/T-DM1 cells to the HER2-positive cancer cells. Cancer cells were co-incubated with NK cells, SE-NK/T-DM1 cells, or T-DM1+NK cotreatment at an ET ratio of 10:1. After 30 min, unbound cells were thoroughly washed and the remaining NK cells were counted using flow cytometry to calculate the remaining ET ratio. Cancer cells were labeled in red with CellTracker Red CMTPX and NK cells were labeled in blue with CellTracker Blue CMAC. Data represent mean±SD (ns, not significant; ***P<0.0001, by one-way ANOVA with Bonferroni post hoc tests).

Figure 3A:
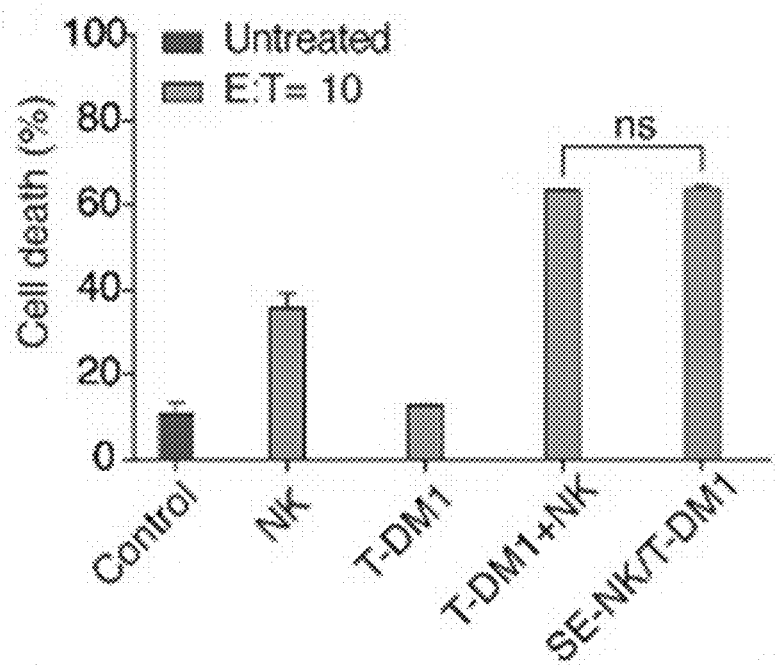
FIG. 3A shows cancer cell death induced by coincubating T-DM1+NK cotreatment or SE-NK/T-DM1 cells with SK-BR-3 cells. Cancer cells labeled with CMAC (blue) dye were incubated with unmodified NK cells, T-DM1, T-DM1+NK cotreatment, or SE-NK/T-DM1 cells for 24 h without removing the unbound NK cells.
Figure 3B:
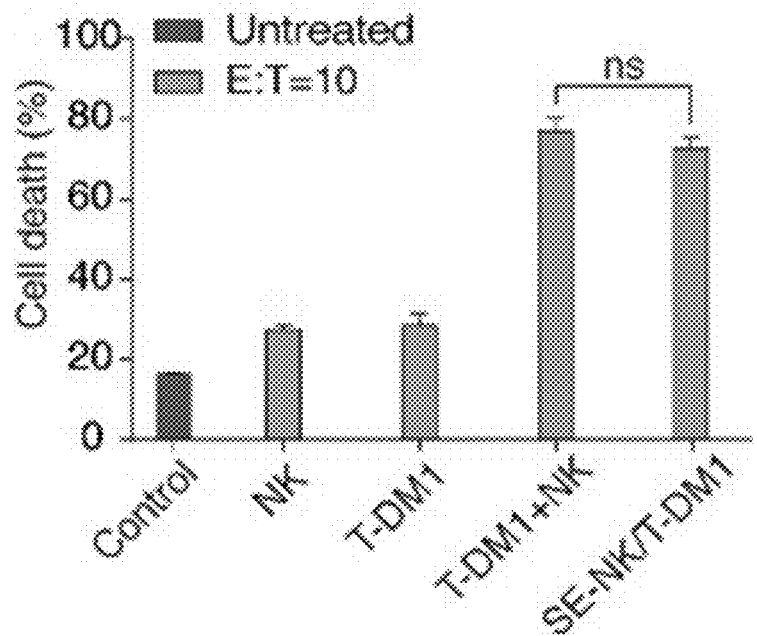
FIG. 3B shows cancer cell death induced by coincubating T-DM1+NK cotreatment or SE-NK/T-DM1 cells with Calu-3 cells. Experimental details are the same as in FIG. 3A above.
Figure 3C:
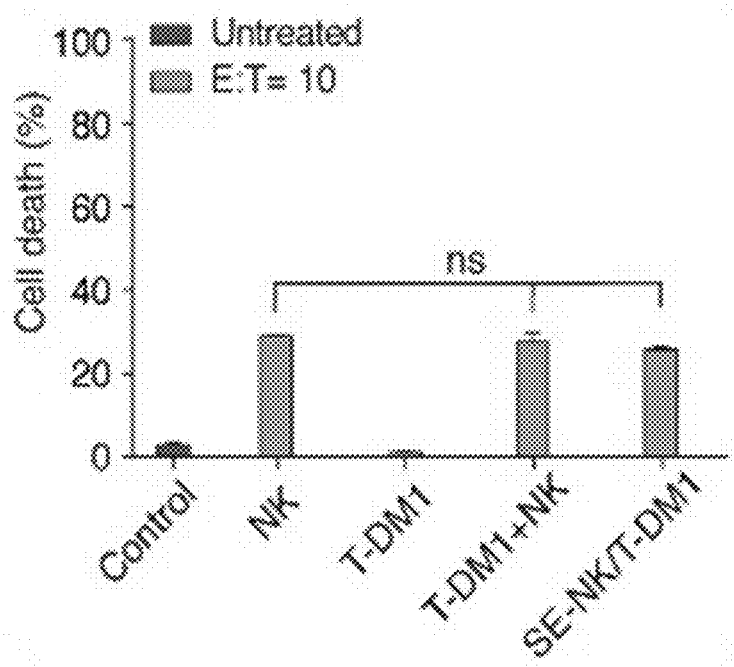
FIG. 3C shows cancer cell death induced by coincubating T-DM1+NK cotreatment or SE-NK/T-DM1 cells with MDA-MB-231 cells. Experimental details are the same as in FIG. 3A.
Figure 3D:
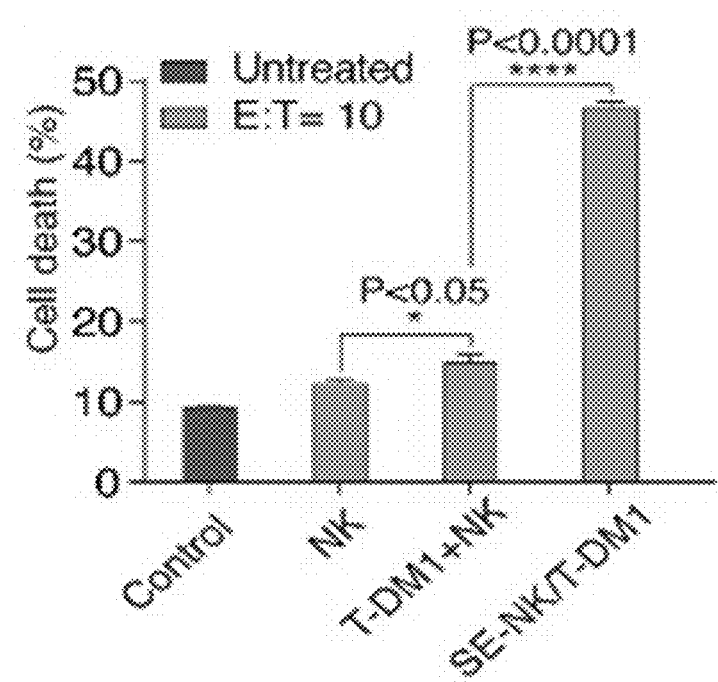
Figure 3E:
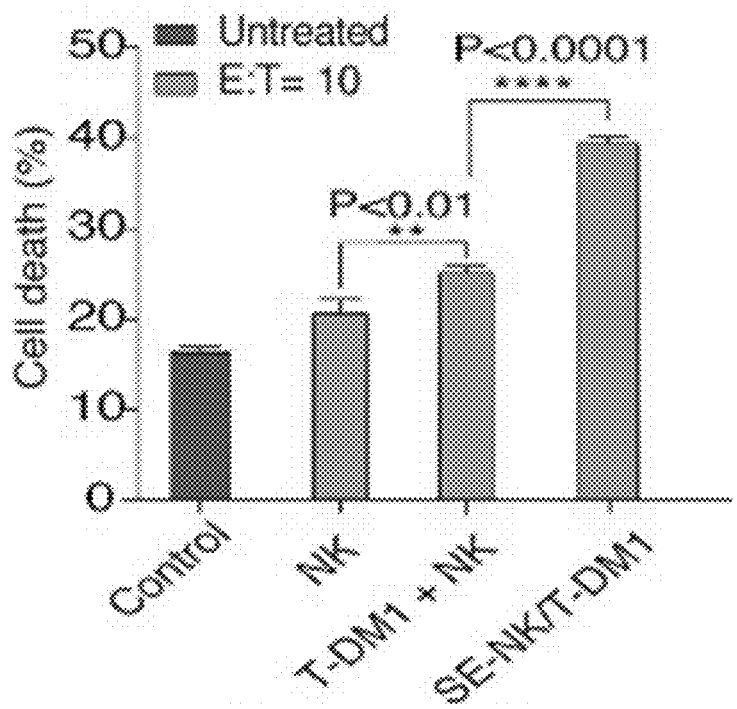

FIG. 3D shows targeted anticancer activity of SE-NK/T-DM1 cells, wherein unbound NK cells were removed after the coincubation of SE-NK/T-DM1 cells with SK-BR-3 cells. Unbound NK cells were removed after 2 h of incubation and the remaining cell mixtures were incubated for additional 24 h. Cancer cell death was measured with flow cytometry using an annexin V Alexa Fluor 488 and propidium iodide kit. Data represent mean±SD (ns, not significant, *P<0.05, P<0.01, **P<0.0001, by two-way ANOVA with Bonferroni post hoc tests), FIG. 3E shows targeted anticancer activity of SE-NK/T-DM1 cells, wherein unbound NK cells were removed after the coincubation of SE-NK/T-DM1 cells with SK-Calu-3 cells.

Figure 3F:
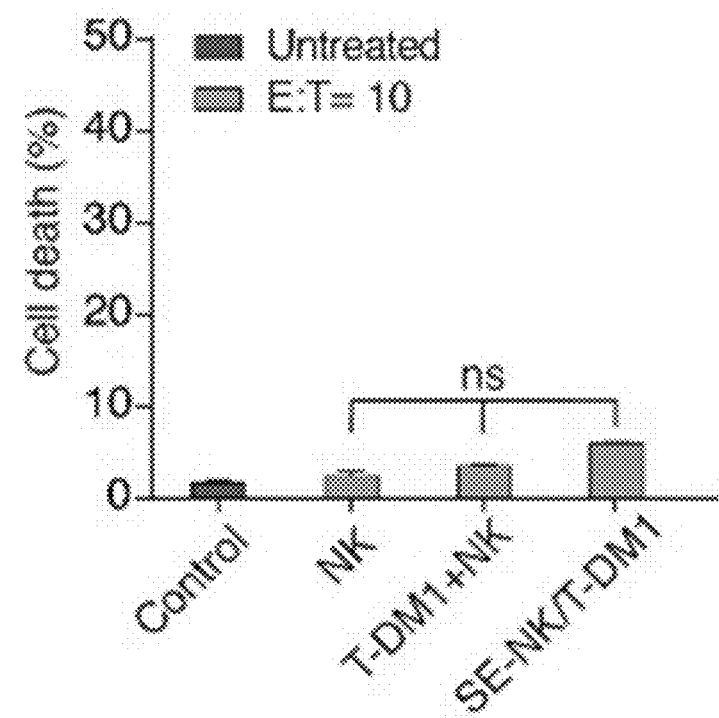

FIG. 3F shows targeted anticancer activity of SE-NK/T-DM1 cells, wherein unbound NK cells were removed after the coincubation of SE-NK/T-DM1 cells with MDA-MB-231 cells.

Figure 4A:
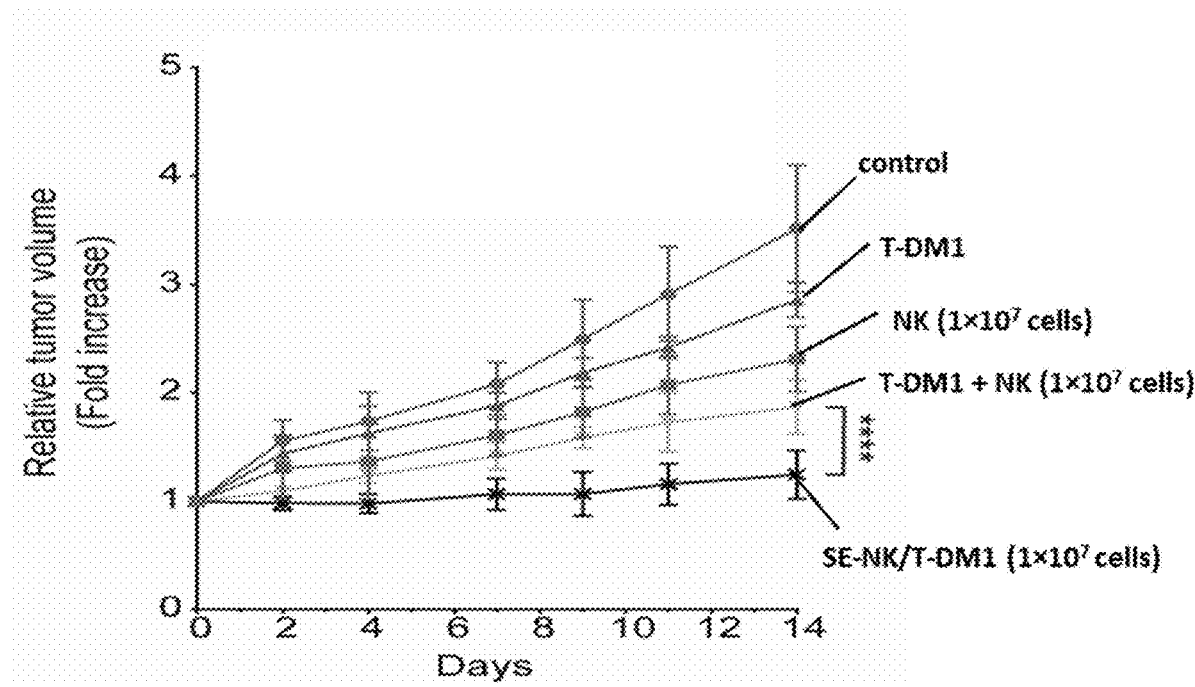

FIG. 4A shows relative tumor volume change of HER2-positive Calu-3 cancer. Tumors were inoculated on the left flank of female NOD scid Gamma (NSG) mice. Tumor-bearing mice received weekly treatment of no treatment, 0.21 mg of T-DM1, 1×107 NK cells, 0.21 mg of T-DM1+1×107 NK cotreatment, or 1×107 SE-NK/T-DM1 cells through tail vein infusion for 14 d. All agents were freshly prepared in 250 μL of PBS and the infusion was scheduled for 1 min. Data represent mean±SD (****P<0.0001, two-way repeated measure ANOVA with Bonferroni post hoc tests).

Figure 4B:
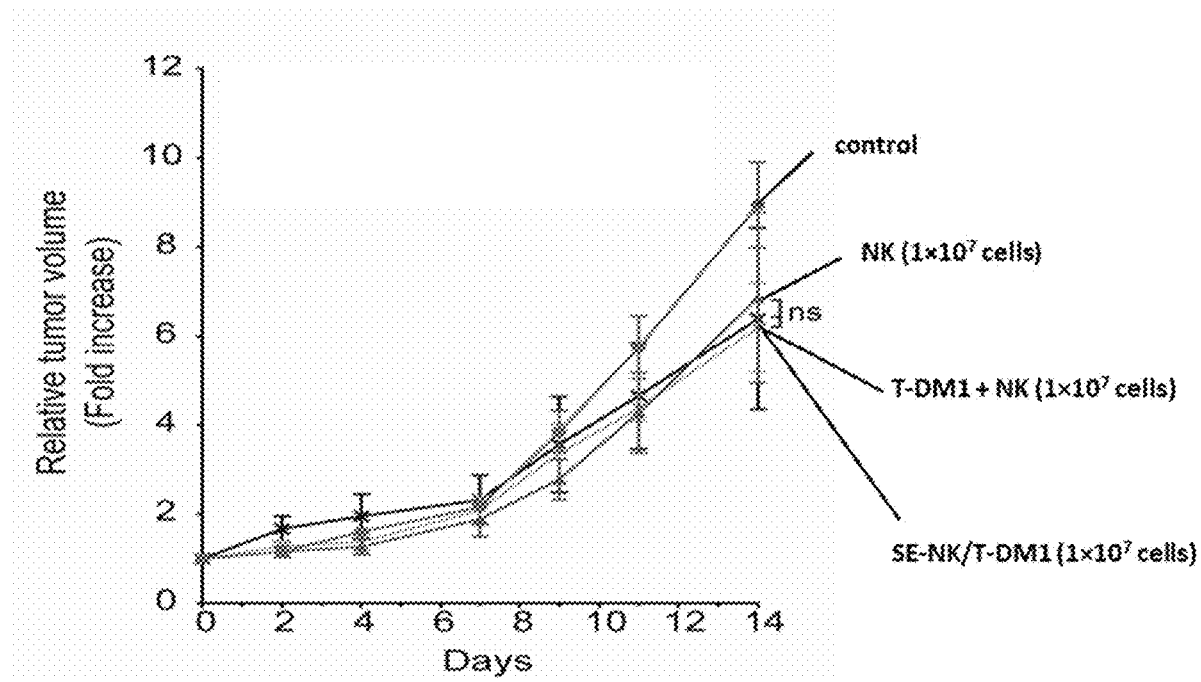

FIG. 4B shows relative tumor volume change of HER2-negative MDA-MB-231 cancer. Experimental details were the same as in FIG. 4A above.

Figure 4C:
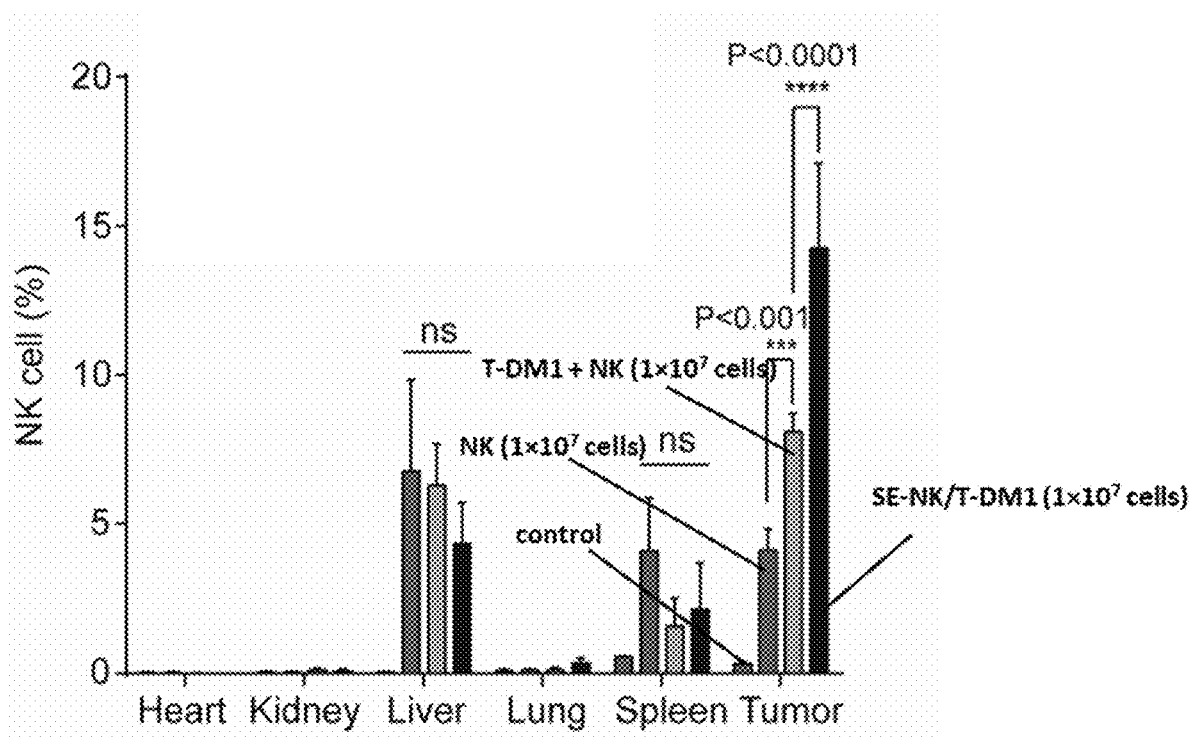

FIG. 4C shows biodistribution of SE-NK/T-DM1 cells in Calu-3 tumor-bearing NSG mice (n=3). Animals received no treatment, 1×107 NK cells, 0.21 mg of T-DM1+1×107 NK cotreatment, or 1×107 SE-NK/T-DM1 cells through tail vein infusion. All agents were freshly prepared in 250 μL of PBS for 1 min infusion. Tumor and other vital organs were harvested at 24 h post-treatment. Single-cell 50 suspension was prepared from the harvest tissues and APC-conjugated anti-CD56 antibodies were applied to detect NK cells. Flow cytometer was used to count NK cells among 1×105 total cells. Data represent mean±SD (ns, not significant; *P<0.001; **P<0.0001; two-way ANOVA with Bonferroni post hoc tests).

TERMS

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. The term "comprising" means that other elements can also be present in addition to the defined elements presented. The use of "comprising" indicates inclusion rather than limitation. Stated another way, the term "comprising" means "including principally, but not necessary solely". Furthermore, variation of the word "comprising", such as "comprise" and "comprises", have correspondingly the same meanings. In one respect, the technology described herein related to the herein described compositions, methods, and respective component(s) thereof, as essential to the invention, yet open to the inclusion of unspecified elements, essential or not ("comprising").

All embodiments disclosed herein can be combined with other embodiments unless the context clearly dictates otherwise. Suitable methods and materials for the practice and/or testing of embodiments of the disclosure are described below. Such methods and materials are illustrative only and are not intended to be limiting. Other methods and materials similar or equivalent to those described herein can be used. All publications, patent applications, patents, and other references mentioned herein are incorporated by reference in their entirety for all purposes. In case of conflict, the present specification, including explanations of terms, will control. Although methods and materials similar or equivalent to those described herein can be used to practice or test the disclosed technology, suitable methods and materials are described below. The materials, methods, and examples are illustrative only and not intended to be limiting. In order to facilitate review of the various embodiments of the disclosure, the following explanations of specific terms are provided:

Antibody and Antibody Fragment: The term "antibody" herein is used in the broadest sense and encompasses various antibody structures, including but not limited to monoclonal antibodies, polyclonal antibodies, multispecific antibodies (e.g., bispecific antibodies), and antibody fragments. "Antibody" can refer to a peptide (e.g., polypeptide) that includes at least a light chain or heavy chain immunoglobulin variable region and specifically binds an epitope of an antigen. An antibody can be conjugated. An antibody can be labeled with a detectable label, such as an enzyme, hapten, or fluorophore. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Antibody Drug Conjugate (ADC): An "antibody-drug conjugate" refers to a substance comprising a monoclonal antibody chemically linked to a drug, such as a cytotoxic compound. The monoclonal antibody binds to a specific target, such as a protein or receptor found on certain types of cells. The linked drug may enter and destroy the targeted cell. ADCs are typically used as targeted therapy for treatment of cancer.

Effective Amount: The term "effective amount," as used herein, refers to a dosage of a compound or a composition effective for eliciting a desired effect. This term as used herein may also refer to an amount effective at bringing about a desired in vivo effect in an animal, mammal, or human.

Monoclonal Antibody and Polyclonal Antibody: The term "monoclonal antibody" refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. The term "polyclonal antibody" refers to an antibody preparation that typically includes different antibodies directed against different determinants (epitopes). In contrast to a polyclonal antibody, each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any particular method. Monoclonal antibodies (mAbs) have been established as a mainstream mode of immunotherapy as well as vehicles for targeted delivery of cytotoxic agents.

Specific for: As used herein, the phrase "specific binding," "specifically binds to," or "specific for" refers to measurable and reproducible interactions such as binding between a target and a biomarker-specific agent, which is determinative of the presence of the target in the presence of a heterogeneous population of molecules including biological molecules. For example, a binding entity that specifically binds to a target may be an antibody that binds this target with greater affinity, avidity, more readily, and/or with greater duration than it binds to other targets.

Subject: As used herein, the term "subject" is intended to include human and non-human animals. The term "non-human animals" includes all vertebrates, e.g. non-mammals (such as chickens, amphibians, reptiles), and mammals, such as non-human primates, domesticated and/or agriculturally useful animals (such as sheep, dogs, cats, cows, pigs, etc.), and rodents (such as mice, rats, hamsters, guinea pigs, etc.).

Targeting moiety: The term "targeting moiety" refers to any chemical entity that serves to bind or target or direct the modified cell (e.g., immune cell) to a particular location or association, e.g., the targeting moiety may be an antibody or fragment thereof that binds the immune cell to a target such as a biomarker on the surface of a target cell. A targeting moiety may, for example, be used to direct a modified cell to a specific protein or enzyme, or to a particular cellular location, or to a particular cell type. A targeting moiety may be used to help selectively enhance accumulation of the modified cell. Suitable targeting moieties include, but are not limited to proteins, peptides, glycoproteins, glycopeptides, steroids, polysaccharides, hormones, cofactors, nucleic acids, antibodies, chimeric antigen receptors, and drugs.

Treatment: As used herein, the terms "treat" or "treatment" or "treating" refers to both therapeutic treatment and prophylactic or preventative measures, wherein the object is to prevent or slow the development of the disease, such as slow down the development of a cardiac disorder, or reducing at least one adverse effect or symptom of a condition, disease or disorder, e.g., any disorder characterized by insufficient or undesired function. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with a condition, as well as those likely to develop a condition due to genetic susceptibility or other factors such as weight, diet and health.

DETAILED DESCRIPTION OF THE INVENTION

Surface Engineered Immune Cells

The present invention features compositions that combine chemotherapy and immunotherapy for the development of targeted cancer chemoimmunotherapy. The compositions herein comprise a targeting moiety-drug complex (e.g., antibody-drug conjugate (ADC)), which is attached to an immune cell via a phospholipid-polyethylene glycol (PEG) linker. For example, the targeting moiety-drug complex (e.g., ADC) may be attached to the immune cell by incorporating the phospholipid-PEG linker into the lipid bilayer of the immune cell.

As previously discussed, the present invention is not limited to the targeting moiety-drug complexes (e.g., ADCs) described herein, such as those featuring T-DM1. Any appropriate targeting moiety-drug complexes, including those currently marketed and undergoing development, can be incorporated on the surface of an immune cell (e.g., any immune cell) using the methods and compositions described herein.

In some embodiments, the immune cell is a natural killer (NK) cell. However, the present invention is not limited to NK cells. In some embodiments, the immune cell is a lymphocyte, e.g., a T cell (e.g., killer T cell, a helper T cell, a Gamma delta T cell, etc.), a B cell, etc. In some embodiments, the immune cell is a leukocyte. In some embodiments, the immune cell is a phagocyte, e.g., a neutrophil, a macrophage, a monocyte, a mast cell, etc. The present invention is not limited to the aforementioned cells.

The targeting moiety-drug complex comprises a targeting moiety (or binding moiety) that is specific for a particular cell marker or a cancer cell. The targeting moiety may be, for example, an antibody or an antibody fragment. However, the present invention is not limited to antibodies or fragments thereof. The targeting moiety may include any chemical entity capable of specifically binding a target. Suitable targeting moieties may include, but are not limited to proteins, peptides, glycoproteins, glycopeptides, steroids, polysaccharides, hormones, cofactors, nucleic acids, antibodies, chimeric antigen receptors and drugs. Likewise, the target may be any ligand capable of specific binding to the targeting moiety.

As an example, in certain embodiments, the targeting moiety is an anti-HER2 targeting moiety (e.g., anti-HER2 antibody such as trastuzumab), e.g., a targeting moiety specific for HER2. HER2 is a cell marker overexpressed on the surface of certain types of cancer cells, e.g., breast cancer cells. Targeting moieties may include but are not limited to alemtuzumab, pertuzumab, bevacizumab, rituximab, abciximab, adalimumab, alefacept, basiliximab, belimumab, bezlotoxumab, canakinumab, certolizumab pegol, cetuximab, daclizumab, denosumab, efalizumab, golimumab, inflectra, ipilimumab, ixekizumab, natalizumab, nivolumab, olaratumab, omalizumab, palivizumab, panitumumab, pembrolizumab, tocilizumab, trastuzumab, secukinumab, ustekinumab, etc. Thus, the cell marker that the targeting moiety targets includes (but is not limited to) any of the cell markers that the aforementioned antibodies target. In certain embodiments, the targeting moiety may be an anti-CD53 antibody, an anti-CD30 antibody, an anti-CD20 antibody, an anti-Ep-CAM antibody, an anti-VEGF antibody, an anti-VEGFR antibody, an anti-MSLN antibody, an anti-CD319 antibody, an anti-phosphatidylserine antibody, an anti-FGFR antibody (e.g., anti-FGFR2 antibody), an anti-CD44 antibody, an anti-Notch1 antibody, an anti-mucin antibody, an anti-MCP-1 antibody, an anti-Lewis-Y antigen antibody, an anti-PCDC1 antibody, an anti-IL2 antibody, an anti-EGFR antibody, an anti-CEACAM5 antibody, an anti-MUC1 antibody, an anti-glypican 3 antibody, an anti-PTK7 antibody, an anti-CD19 antibody, an anti-RANKL antibody, an anti-B lymphoma cell antibody, an anti-DR5 antibody, an anti-CLDN19 antibody, an anti-HERS antibody, an anti-HER1 antibody, an anti-CD4 antibody, an anti-CD70 antibody, etc.

The targeting moiety-drug complex further comprises a drug, such as a cytotoxic drug. Non-limiting examples of drugs that may be used according to the present invention include emtansine (DM1), Brentuxmab vedotin, Gemtuzumab oozogamicin, Inotuzumab ozogamicin, Trastuzumab emtansine, BT-062, CDX-011, Milatuzumab-dox, SAR3419, AGS-16M8F, ASG-22ME, ASG-SME, BAY 79-4620, BAY 94-9343, BIIB015, IMGN529, IMMU-130, Lorvotuzumab mertansine, MDX-1203, PSMA ADC, RG7593, SAR566658, SGC-75, etc. The targeting moiety-drug complex is linked or attached to the immune cell via a phospholipid-PEG linker. The phospholipid-PEG linker may be conjugated to the targeting moiety. In certain embodiments, the phospholipid-PEG linker is pre-conjugated to the targeting moiety (e.g., targeting moiety-drug complex), e.g., the targeting moiety-drug complex. In certain embodiments, the present invention provides the phospholipid-PEG linker separate from the targeting moiety-drug complex. The phospholipid may be any suitable phospholipid capable of hydrophobically binding to the surface of a cell. For example, the phospholipid may include, but is not limited to: 1,2-dimyristoyl-sn-glycero-3-phosphoethanolamine (DMPE), 1,2-dipalmitoyl-sn-glycero-3-phosphoethanolamine, and 1,2-distearoyl-sn-glycero-3-phosphocholine. In some embodiments, the phospholipid may be 1,2-dimyristoyl-sn-glycero-3-phosphoethanolamine (DMPE). The polyethylene glycol (PEG) may have a molecular weight from 1 kDa to 20 kDa. In certain embodiments, the PEG has a molecular weight from 2 kDa to 10 kDa, e.g., 2 kDa, 3 kDa, 4 kDa, 5 kDa, 6 kDa, 7 kDa, 8 kDa, 9 kDa, 10 kDa. In certain embodiments, the PEG has a molecular weight from 4.5 kDa to 5.5 kDa (e.g., 5 kDa).

The composition may comprise the targeting moiety-drug complex linked to the phospholipid-PEG linker. In certain embodiments, the composition comprises the targeting moiety-drug complex and the immune cell, e.g., the composition may comprise the immune cell and the targeting moiety-drug complex linked to the immune cell via the phospholipid-PEG linker.

Methods

The present invention also features methods of preparing compositions of the present invention, e.g., methods of preparing the targeting moiety-drug complex, methods of linking the targeting moiety-drug complex to cells such as immune cells, etc. As an example, a DMPE-PEG-ADC (e.g., polyethylene glycol (PEG) linking 1,2-dimyristoyl-sn-glycero-3-phosphoethanolamine (DMPE) to an antibody-drug conjugate (ADC)) may be prepared as a ready-to-use formulation. Immune cells, such as pre-expanded immune cells, may be transformed to a targeted form of chemoimmunotherapy by mixing immune cells and DMPE-PEG-ADC together for a time period (e.g., any appropriate time period, e.g., 15 minutes). Immune cells equipped with ADCs can migrate toward the target tumor site through the recognition of target antigen by ADCs. In the target tumor tissues, ADCs induce apoptosis of the target cancer cells and immune cells present in proximity destroy the dying cancer cells that expressed damage-associated molecular patterns (DAMP).

The present invention also features methods of use of the compositions of the present invention, e.g., methods of use of the surface engineered cells with the targeting moiety-drug complex. The present invention also features adoptive transfer of immune cells, e.g., adoptive transfer of compositions of the present invention that comprise surface engineered immune cells as described herein. The present invention also features methods of targeted chemoimmunotherapy. The present invention also features methods of treating a disease or condition in a subject in need thereof, e.g., methods of treating a tumor.

With respect to the preparation of compositions herein, certain compounds described herein may be commercially available. Others may need synthetic preparation.

In certain embodiments, the phospholipid-PEG carries a reactive functional group on the terminus of the PEG, which may be used for coupling with a targeting moiety-drug complex. For example, when the reactive functional group is NHS, the intermediate may couple with a targeting moiety that has a reactive amino group to form an amide. When the reactive functional group is an amine, the intermediate may couple with a reactive isothiocyanate to form a thiocarbamate. When the reactive functional group is an azide, the intermediate may couple with targeting moieties that have a reactive nitrile or a reactive alkyne group to form a tetrazole or a triazole. When the reactive functional group is maleimide, the intermediate may couple with a targeting moiety that has a reactive thiol group to form a bond between the sulfur of the thiol and carbon of the resulting succinimide.

As can be appreciated by the skilled artisan, further methods of synthesizing the compounds herein will be evident to those of ordinary skill in the art. Additionally, the various synthetic steps may be performed in an alternate sequence or order to give the desired compounds. Synthetic chemistry transformations and protecting group methodologies (protection and de-protection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents or Organic Synthesis, John Wiley and Sons (1995), and subsequent editions thereof.

With respect to surface modification of immune cells, in certain embodiments, surface modification of a cell may be achieved by the phospholipid portion of the compound interacting with, and binding to the lipid bilayer membrane of the cell. Each component, or variable, of the composition may be evaluated to determine preferred components and their ability to modify the surface of a cell. For example, compositions possessing differing molecular weights of PEG may be utilized to determine which PEG size is preferable for the interaction between the phospholipid and cell membrane. The choice of reactive functional group attached to the terminus of the PEG may also be evaluated, depending on the targeting moiety being attached and the compatibility of the reactive functional groups it possesses. In addition, the minimum incubation time with the cell, along with the optimized quantity of the compound required for cell modification may also be determined.

Experiments that may determine certain abilities of the surface modified (or surface engineered) cells may be conducted. These may include experiments focused on cell adhesion, toxicity, proliferation, and recovery rate. In addition, kinetic experiments may determine the length of time that the compound can remain immobilized on the surface of the cell. Additionally, the use of different targeting moieties may be evaluated to determine their effect on the ability to modify the cell. Different fluorescent chemical entities, such as fluorescein isothiocyanate (FITC) and green fluorescent protein (GFP), may also be attached to or replace the targeting moiety for evaluation of the composition's ability to modify the cell.

Evaluation of the binding of a target (e.g., receptor of a cell of interest) to a targeting moiety on the surface of an immune cell may be achieved by various means. As an example, in certain embodiments, evaluation of the binding of the target to the targeting moiety on the surface of an immune cell may involve incubating a fluorescent-labeled target ligand with a cell modified by a composition herein that contains a fluorescent-labeled targeting moiety. Migration of cells modified with a composition herein toward the gradient of an appropriate target (e.g., receptor of a cell of interest) may be achieved by incubation of the modified immune cell with the target. Evaluation of the modified cell's ability to migrate may be determined by appropriate cell counting assays or other appropriate means.

The methods described herein include methods of treating disease states in a subject in need of treatment. Such methods may comprise administering to the subject a therapeutically effective amount of a composition described herein. The composition for administration to the subject in need may be comprised of immune cells engineered to carry a targeting moiety-drug complex, wherein the targeting moiety is specific for a particular cell of interest. Also described herein are methods of promoting in vivo homing of the described composition to a target of a cell of interest, wherein the targeting moiety may bind or interact with a target of the cell of interest, e.g., a cell that is associated with a particular diseased tissue, and the modified cell may be recruited to the diseased tissue.

It will be appreciated that appropriate dosages of the compositions herein can vary from patient to patient. Determining the optimal dosage will generally involve the balancing of the level of therapeutic benefit against any risk or deleterious side effects of the treatments described herein. The selected dosage level will depend on a variety of factors including, but not limited to: the activity of the particular composition, the route of administration, the time of administration, the rate of excretion of the composition (e.g., the drug portion), the duration of the treatment, other drugs, compounds, and/or materials used in combination, and the age, sex, weight, condition, general health, and prior medical history of the patient. The amount of compound and route of administration may be at the discretion of the physician, although generally the dosage will be to achieve local concentrations at the site of action that achieve the desired effect without causing substantial harmful or deleterious side-effects.

In certain embodiments, administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

The present invention also features kits for modifying immune cells according to the present invention. In some embodiments, the kit comprises a phospholipid-PEG linker, a targeting moiety-drug complex, and reagents for linking the phospholipid-PEG linker to the targeting moiety-drug complex. In some embodiments, the kit comprises a targeting moiety-drug complex already linked with the phospholipid-PEG linker. In some embodiments, the kit further comprises immune cells. Any combination of one or more of the components used in the present invention, e.g., cells, targeting moieties, linkers, drugs, reagents, etc., may be combined to form a kit.

Example

The following Example describes the production and use of surface engineered Natural Killer cells specific for HER2. The present invention is not limited to the methods and compositions described herein. Briefly, trastuzumab emtansine (T-DM1), a model ADC, was first modified by attaching 1,2-dimyristoyl-sn-glycero-3-phosphoethanolamine (DMPE) conjugated polyethylene glycol (PEG), and the resulting hydrophobized T-DM1 (DMPE-PEG-T-DM1) was used to modify the surface of allogeneic natural killer (NK) cells, a model immune cell. These T-DM1 surface-engineered NK (SE-NK/T-DM1) cells recognized and destroyed human epidermal growth factor receptor 2 (HER2)-positive cancer cells through the combined activity of T-DM1 and NK cells. This single-injection formulation chemoimmunotherapy, SE-NK/T-DM1 cells, suppressed the progression of the target tumor significantly compared to the cotreatment of NK cells and T-DM1.

Surface Engineering of Immune Cells: NK cells and JK cells were 3 modified with DMPE-PEG-T-DM1 or DMPE-PEG-TZ to generate SE-NK/T-DM1 cells, SE-NK/TZ cells, and SE-JK/T-DM1 cells, Briefly, $5 \times 10^5$ immune cells were incubated with different amounts of DMPE-PEG-T-DM1 or DMPE-PEG-TZ in 100 µL PBS at room temperature for 15 min. After the modification, cells were washed twice with 1 mL PBS. The one-step method was optimized with 100 µg of DMPE-PEG-T-DM1 per $5 \times 10^5$ immune cells.

Characterization of Surface-Engineered Cells: SE-NK/T-DM1 cells were prepared with FITC-labeled DMPE-PEG-T-DM1 according to the procedure described above. SE-NK/T-DM1-FITC cells were visualized by confocal microscopy (Nikon AIR, Nikon; Ex/Em=495/520 nm). Collected images were processed with ImageJ software. Changes in cell viability and proliferative functions following the modification were determined using CCK-8. Surface retention times of T-DM1 on the SE-NK/T-DM1 cell membrane were measured using Alexa 488-conjugated goat anti-human (H+L) antibodies (Ex/Em=495/520 nm). SE-NK/T-DM1 cells incubated in complete growth media were withdrawn at each time point and labeled with 10 µg of Alexa 488-conjugated goal anti-human (H+L) antibodies. Fluorescent signals were measured by flow cytometry and analyzed by FlowJo software. The availability of NK cells receptors after the surface engineering was tested using APC-conjugated anti-CD56 antibodies (Ex/Em=650/660 nm) or APC-conjugated anti-2B4 antibodies (Ex/Em=650/660 nm). Each antibody was applied onto SE-NK/T-DM1-FITC cells according to the manufacturer's recommended amount. The availability of CD56 and 2B4 on SE-NK/T-DM1 was detected by flow cytometry and analyzed by FlowJo software.

Selective Binding, Transfer, and Internalization of T-DM1: SK-BR-3 27 cells, Calu-3 cells, and MDA-MB-231 cells were labeled with $2 \times 10^{-6}$ m 28 of CellTracker Red CMTPX (Ex/Em=577/602 nm). Cancer cells were seeded on 24-well plate at a density of $4 \times 10^4$ cells/well 24 h prior to treatment. NK cells were labeled with $1 \times 10^{-6}$ m of CellTracker Blue CMAC (Ex/Em=353/466 nm) prior to surface engineering with DMEP-PEG-T-DM1. Cancer cells were coincubated with unmodified NK cells, T-DM1±NK cotreatment, and SE-NK/T-DM1 cells at an E:T ratio of 10:1, After 30 min, unbound NK cells were removed and all remaining cells were collected. The number of NK cells was quantified per $1 \times 10^4$ cancer cells by flow cytometry and the remaining E:T ratio was calculated. Transfer of T-DM1 from SE-NK/T-DM1 cells to target cancer cells was examined using confocal microscopy. SK-BR-3 cells, Calu-3 cells, and MDA-MB-231 cells labeled with $2 \times 10^{-6}$ m of CellTracker Red CMTPX and seeded on a Lab-Tek II eight-chambered cover glass slide at a density of $1 \times 10^4$ cells/well 24 h prior to treatment. NK cells labeled with $1 \times 10^{-6}$ m CellTracker Blue CMAC were modified with 100 µg of DMPE-PEG-T-DM1-FITC, After the modification, $1 \times 10^5$ SE-NK/T-DM1 cells were coincubated with the cancer cells for 30 min and washed with PBS to remove the unbound effector cells, Coincubated cells were imaged by confocal microscopy and collected images were processed by ImageJ software, Internalization of T-DM1 was visualized using a similar procedure. Cancer cells labeled with NucBlue Live ReadyProbe Reagent (Ex/Em=360/460 nm) were seeded on a Lab-Tek II eight-chambered cover glass at a density of $1 \times 10^4$ cells/well 24 h prior to treatment. NK cells labeled with $1 \times 10^{-6}$ m CellTracker Red CMTPX were modified with 100 µg of DMPE-PEG-T-DM1-FITC. Cancer cells were treated with T-DM1-FITC or CMPTX-labeled SE-NK/T-DM1-FITC cells at an E:T ratio of 10:1. Unbound T-DM1-FITC and SE-NK/T-DM1-FITC cells were thoroughly removed after 30 min. Internalization of T-DM1-FITC (Ex/Em=495/520 nm) was imaged using confocal microscopy at the initial time point and 6 h later. Collected images were processed with ImageJ software.

Cancer-Targeted Cytotoxicity of SE-NWT-DV, Cells: SK-BR-3 cells, Calu-3 cells, and MDA-MB-231 cells were labeled with $2 \times 10^{-6}$ m of CellTracker Blue CMAC and seeded at a population of $1 \times 10^4$ cells/well on a 48-well plate 24 h prior to treatment. Cancer cells were coincubated with unmodified JK cells, unmodified NK cells, TZ, T-DM1, T-DM1+JK cotreatment, T-DM1+NK cotreatment, SE-NK/T-DM1 cells, SE-NK/TZ cells, or SE-JK/T-DM1 cells at an E:T ratio of 10:1 in 600 µL of complete media. Cancer cells receiving T-DM1 treatment received 2.1 µg of T-DM1 that corresponds to the T-DM1 amount on SE-NK'T-DM1 treated at an E:T ratio of 10:1. All treatments were washed 2 h after the coculture, and the remaining cancer-bound effector cells were further incubated for 24 h. All cells were harvested and labeled with the Annexin V Alexa Fluor 488 and propidium iodide kit (Annexin Ex/Em=495/520 nm and propidium Ex/Em=535/617) after 24 h of coincubation. Cancer cell death was analyzed by flow cytometry. To distinguish the effects of antibodies, chemotherapeutic agents, and immune cells, cancer cells labeled with CMAC were coincubated with SE-NK/T-DM1 cells, SE-NK/TZ cells, SE-JK/T-DM1 cells, or other corresponding treatments at E:T ratio of 10:1 in 600 µL of complete media. Unbound effector cells were removed 2 h after the initial coincubation and the remaining cell mixtures were further incubated for 24 h. Cancer cells receiving T-DM1 treatment received 2.1 µg of T-DM1 that corresponds to the T-DM1 amount on surface-engineered immune cells with ADCs treated at an E:T ratio of 10:1. Resulting cancer cell death was identified with Annexin V Alexa Fluor 488 and propidium iodide kit (Annexin Ex/Em=495/520 nm and propidium Ex/Em=535/617) using flow cytometry and analyzed by FlowJo software.

In Vivo Tumor Efficacy and Biodistribution: In vivo studies were conducted with six-week-old female NOD scid gamma (NSG, NOD. Cg-Prkdcscid Il2rgtm1WjI/SzJ) mice purchased from the Jackson Laboratory (Bar Harbor, ME). Each mouse was subcutaneously inoculated with $1\times10^7$ cells of Calu-3 cells or MDA-MB-231 cells on the left flank. Cancer cells were suspended in PBS supplemented with 10% (v/v) Matrigel (Fisher Scientific, Bedford, MA). Tumor volume was recorded three times per week by measuring the length and the width of the tumor with a caliper and calculating the tumor volume on the basis of the following formula: V=0.5ab2, using the longest (a) and shortest (b) diameters of the tumor. When the tumor volume reached $\approx 100$ mm$^3$, tumor-inoculated mice were randomly assigned to the experimental groups. Control group (n=4 for Calu-3 model, n=3 for MDA-MB-231 model) received no treatment but the study groups (n=4 per group) were weekly administrated with 0.21 mg of T-DM1, $1\times10^7$ NK cells, 0.21 mg of T-DM1+$1\times10^7$ NK cotreatment, or $1\times10^7$ SE-NK/T-DM1 cells through tail vein infusion for two weeks (Day 0 and Day 7). All agents were freshly prepared in 250 µL of PBS and the infusion was completed in 1 min. Tumor growth and body weight were monitored for 14 d and relative tumor volume was calculated by dividing the recorded volume with the initial volume. For biodistribution, NSG mice-bearing Calu-3 tumors (n=3) received no treatment, $1\times10^7$ NK cells, 0.21 mg of T-DM1+$1\times10^7$ NK cotreatment, or $1\times10^7$ SE-NK/T-DM1 cells through tail vein infusion. All agents were freshly prepared in 250 µL of PBS for 1 min infusion. Tumor and major organs, including heart, kidneys, liver, lungs, and spleen, were harvested 24 h after the treatment. Single-cell suspension of each harvested organ was prepared using the gentleMACS Dissociator and tissue dissociation kits (Miltenyi Biotec, Bergisch Gladbach, Germany) following the instructions provided by the manufacturer. Half of each cell mixture was incubated with 30 µg of an APC-conjugated anti-CD56 (Ex/Em=650/660 nm) antibody for 1 h at 4° C. Resulting cell mixtures were washed twice with cold PBS and the presence of NK cells were detected from counting $1\times10^5$ total cells by flow cytometry. Collected results were analyzed by FlowJo.

Experimental Results

Figure 1A:
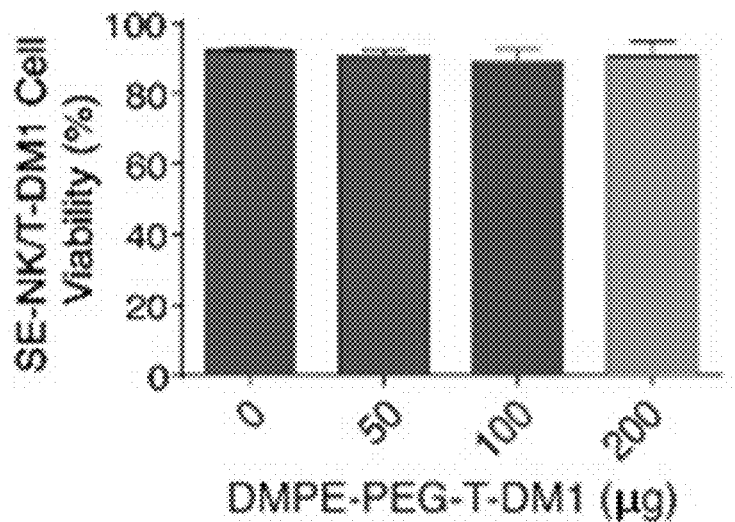
Figure 1B:
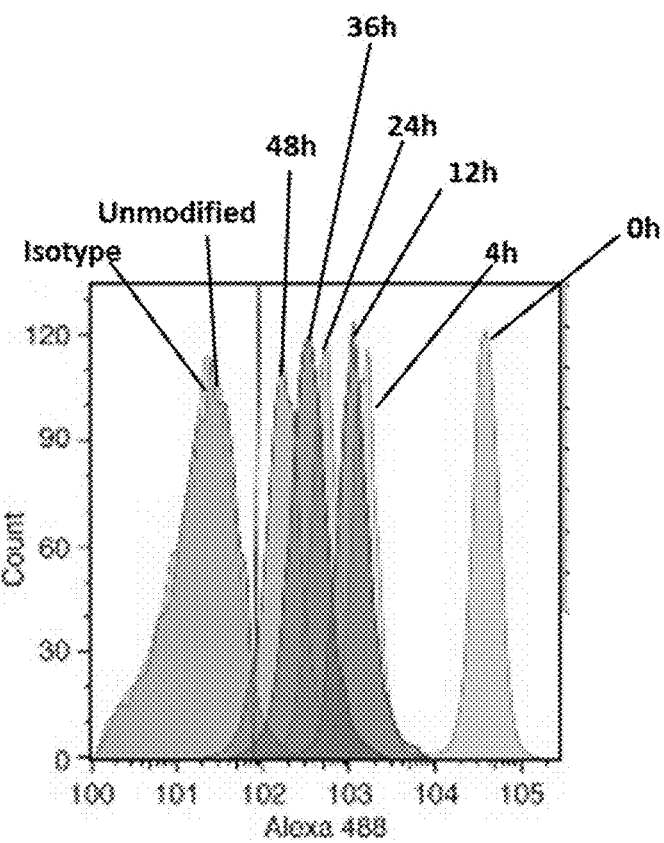
Figure 1C:
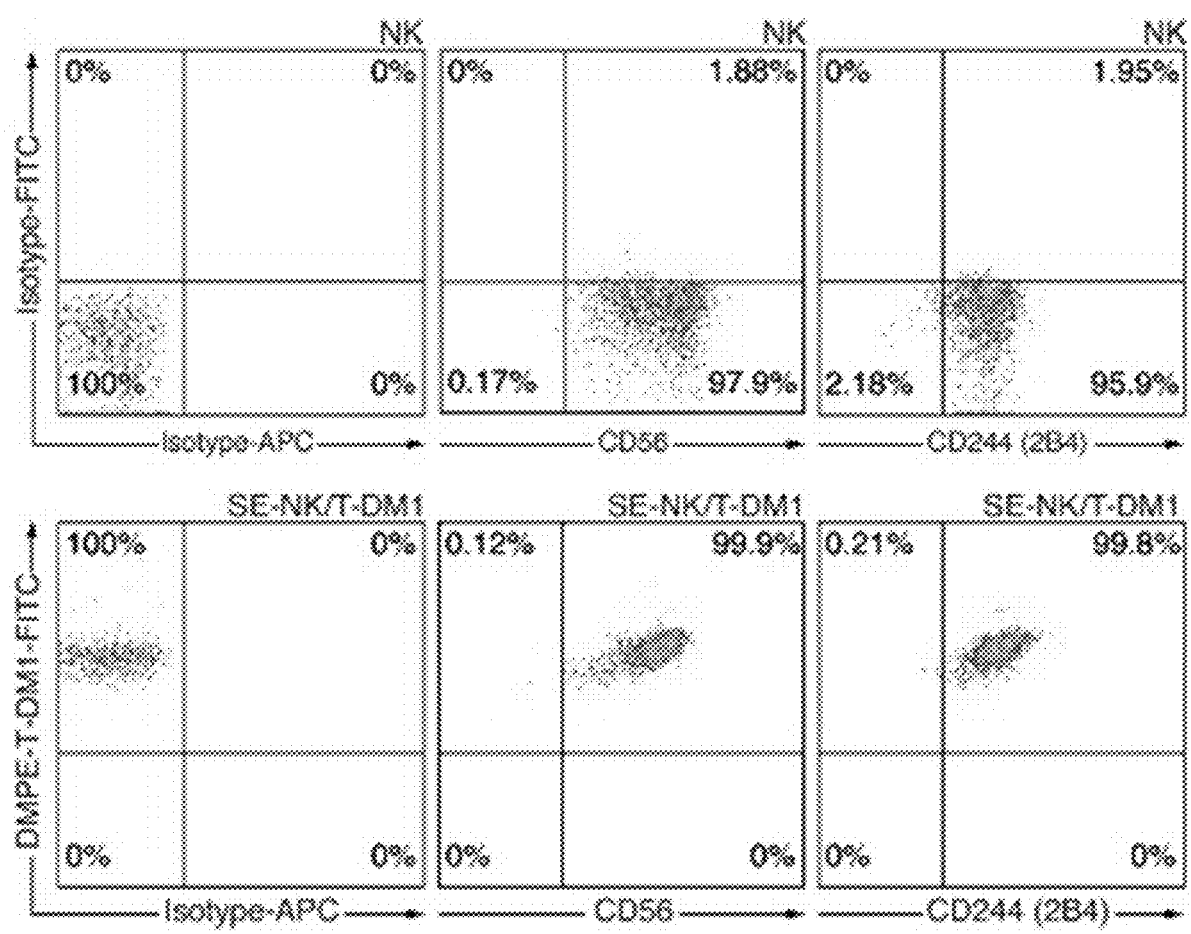

T-DM1 was generated through the expression of trastuzumab (TZ) in mammalian cells followed by DM1 conjugations. Prepared T-DM1 was subsequently hydrophobized by attaching DMPE-PEG-NHS, resulting in the production of DMPE-PEG-T-DM1. The T-DM1 synthesized exhibited similar cytotoxicity compared to the commercial product, Kadcyla. Surface engineering of NK cells with various amounts of DMPE-PEG-T-DM1 affects neither the viability of NK cells (see FIG. 1A), nor the proliferative activity of NK cells. Reliable modification of $5\times10^5$ immune cells required 100 µg of DMPE-PEG-T-DM1 that yielded $\approx 2.1$ µg of T-DM1 embedded on the cell membrane of $1\times10^5$ SE-NK/T-DM1 cells. T-DM1 was detected on the surface of SE-NK/T-DM1 cells for over 48 h in complete growth media (see FIG. 1B) and two of the key NK cell-specific markers, CD56 and 2B4, were available on the surface of SE-NK/T-DM1 cells. These results demonstrate that T-DM1 is embedded on the NK cell surface without internalization and the surface engineering of NK cells with ADCs does not interfere with the NK cell receptor accessibility, suggesting that the inherent cytolytic activity of NK cells is retained upon the surface engineering (see FIG. 1C). Because the allogeneic NK cells used in this study, NK-92 cells, lack CD16, CD32, and CD64 IgG receptors that can initiate antibody internalization and antibody-dependent cellular cytotoxicity (ADCC), the surface engineering with T-DM1 appears to have minimal effects on NK cell metabolism and viability. In cancer cells, T-DM1 internalization occurs through HER2 receptor-mediated endocytosis. NK cells do not express HER2 on their membrane, therefore DMPE-PEG-T-DM1 embedded on the surface of SE-NK/T-DM1 cells were not internalized and showed negligible cytotoxicity. Moreover, PEG spacer between the DMEP and T-DM1 provides a physical barrier for internalization. Studies have reported that longer PEG spacers not only inhibit the internalization of biomolecules but also reduce the membrane insertion efficiency by increasing the steric hindrance. The aforementioned membrane insertion efficiency of DMPE-PEG-T-DM1 yielded about 10% due to the presence of long PEG spacer.

Figure 2:
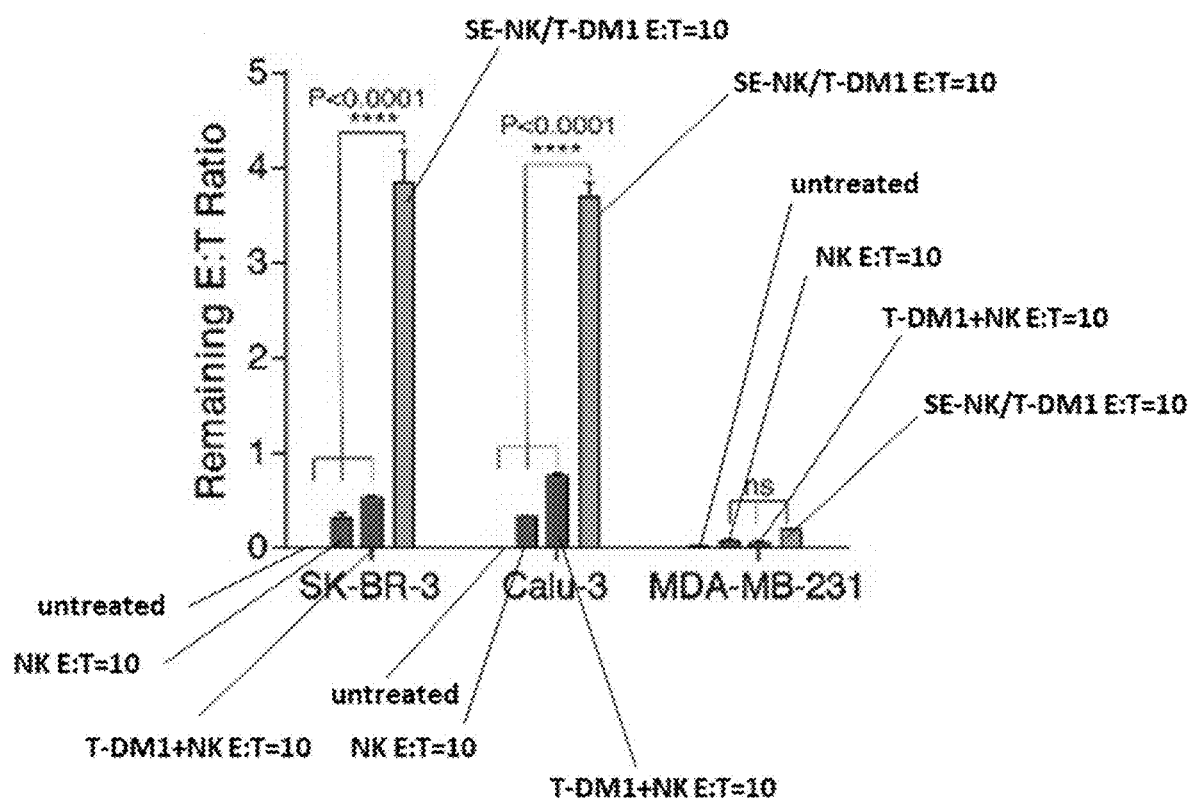

To demonstrate the specific binding of SE-NK/T-DM1 cells to their target cancer cells, the number of remaining NK cells was determined after coincubating SE-NK/T-DM1 cells with the target cancer cells or the nontarget cancer cells. Unmodified NK cells, T-DM1 and NK cells (T-DM1+NK) cotreatment, or SE-NK/T-DM1 cells were incubated with HER2-positive SK-BR-3 cells, HER2-positive Calu-3 cells, or HER2-negative MDA-MB-231 cells at an effector-to-target (E:T) ratio of 10:1 (see FIG. 2). After 30 min of coincubation, unbound NK cells were thoroughly washed and the remaining cells were counted using flow cytometry. The remaining E:T ratios when cancer cells were treated with SE-NK/T-DM1 cells, T-DM1+NK cotreatment, and unmodified NK cells were $\approx 3.8$, 0.5, and 0.3 on SK-BR-3 cells; and, 3.7, 0.8, and 0.3 on Calu-3 cells, respectively. Negligible numbers of NK cells remained bound to MDA-MB-231 cells. These results revealed that SE-NK/T-DM1 cells specifically recognize and bind to HER2-positive cancer cells. In order for T-DM1 to exert its anticancer activity on cancer cells, T-DM1 on the SE-NK/T-DM1 cells must transfer to the target cancer cells. Unmodified NK cells and SE-NK/T-DM1-FITC cells were coincubated with SK-BR-3 cells, Calu-3 cells, or MDA-MB-231 cells on an eight-chambered cover glass sides. Unbound NK cells were removed after 30 min and the transfer of T-DM1-FITC was observed through confocal microscopy. Upon the binding of SE-NK/T-DM1 cells to SK-BR-3 cells and Calu-3 cells, T-DM1 migrated toward the contact area, formed clusters at the effector cell-to-cancer cell junction, and subsequently transferred onto the target cancer cells, Lipids contained in DMPE-PEG-T-DM1 allow the lateral movement of T-DM1 across the NK cell membrane. Through this attribute, DMPE-PEG-T-DM1 was able to polarize toward the contact point between NK cells and cancer cells where HER2 is presented. Once DMPE-PEG-T-DM1 binds to HER2 on cancer cells, these antigen-antibody complexes spread across the cancer cell membrane following lateral movement of HER2 on cancer cells. Polarization of DMPE-PEG-T-DM1, formation of antigen-antibody complex, and transfer of DMPE-PEG-T-DM1 were missing when SE-NK/T-DM1 cells were treated to HER2-negative MDA-MB-231 cells. These results indicate that T-DM1 embedded on the surface of NK cells relocates onto the target cancer cell membrane after forming the antigen-antibody complex.

Internalization of T-DM1 is crucial for its anticancer efficacy because DM1 acts on intracellular targets in cancer cells. In keeping with previously reported observations on cellular uptake of T-DM1, trafficking of T-DM1 to lysosomes, and release of DM1, the focus was on confirming the internalization of T-DM1 transferred from SE-NK/T-DM1 cells in the target cancer cells. Cancer cells plated on an eight-chambered cover glass slide were labeled with nuclear staking dye (blue) to observe the location of FITC-labeled T-DM1 (green) transferred from SE-NK/T-DM1-FITC cells (red). Identical to the study above, unbound NK cells were thoroughly removed after 30 min of coincubation. Distinct fluorescent dots representing the internalized T-DM1, following the transfer from the assessed SE-NK/T-DM1 cells, were detected in the cytoplasm of target cancer cells, representing the internalization of T-DM1 into the target cancer cells. No fluorescent activity was observed in MDA-MB-231 cells treated with the identical conditions used in HER2-positive cancer cells, confirming no internalization of T-DM1 in HER2-negative cancer cells. To validate the therapeutic advantages of SE-NK/T-DM1 cells over the T-DM1+NK cotreatment, the cancer cells were first treated with SE-NK/T-DM1 cells and T-DM1+NK cotreatment for 24 h without the removal of unbound immune cells (see FIG. 3A, FIG. 3B). Both treatments induced similar levels of cancer cell death, indicating that continuous exposure to the T-DM1+NK cotreatment allows enough time for NK cells to identify dying cancer cells affected by T-DM1 in a confined well system. In MDA-MB-231 cells, only the anticancer activity of NK cells was observed in both treatment groups (see FIG. 3C). Subsequently, cancer cells were incubated with the identical treatments for 2 h and the unbound effector cells were removed to mimic the in vivo cancer-targeted homing effect. We further incubated the remaining cancer-bound effector cells with the target cells for 24 h and recorded the resulting cancer cell death. In SK-BR-3 Cells and Calu-3 cells, it was found that the level of cancer cell death induced by SE-NK/T-DM1 cells was greater than that induced by NK cell or T-DM1+NK cotreatment, while no significant cell death was noticed in MDA-MB-231 cells (see FIG. 3D, FIG. 3E, FIG. 3F). This is due to the fact that a higher number of SE-NK/T-DM1 cells remained bound to SK-BR-3 cells and Calu-3 cells, resulting in an augmented level of anticancer activity.

Next, the effect of trastuzumab, DM1, and NK cells, contained in SE-NK/T-DM1 cells on cancer cell viability was assessed. To identify the anticancer effect of DM1, trastuzumab surface-engineered NK (SE-NK/TZ) cells were prepared and the cancer cell death induced by SE-NK/TZ cells and SE-NK/T-DM1 cells was compared. Cancer cell death was analyzed 24 h of coincubation after the removal of unbound NK cells 2 h after the treatment. As expected, T-DM1 exhibited a greater cytolytic effect against SK-BR-3 cells than TZ, The resulting enhanced cancer cell death was due to the addition of DM1. NK cells and TZ (TZ+NK) cotreatment showed slightly improved cytotoxicity compared to the NK cells alone however it was much less compared to the T-DM1+NK cotreatment. The treatments involving T-DM1 further enhanced anticancer activity against HER2-positive cancer cells, and SE-NK/T-DM1 cells exhibited anticancer activity superior to all other treatments. It was postulated that DM1 contained in T-DM1 induced an increase of ≈20% in the death of HER2-positive cancer cells. Except for the nonspecific cytolytic activity of NK cells, none of the treatments induced significant cytotoxicity in MDA-MB-231 cells. NK cells were compared to Jurkat (JK) cells, a surrogate negative T-cell line, in identical experimental settings. Cytotoxicity of T-DM1 surface-engineered JK (SE-JK/T-DM1) cells and SE-NK/T-DM1 cells was tested against SK-BR-3 cells and MDA-MB-231 cells. As expected, NK cells showed higher cytolytic activity in SK-BR-3 cells compared to JK cells, T-DM1+NK cotreatment caused nearly 27% more cancer cell death compared to the T-DM1 with JK cells (T-DM1+JK) cotreatment. Similarly, SE-NK/T-DM1 cells induced ≈58% greater cancer cell death in SK-BR-3 cells compared to SE-JK/T-DM1 cells. Consistently, no significant differences in cell death beyond the NK cell activity were observed in MDA-MB-231 cells. SE-NK/T-DM1 cells did not show augmented cytotoxicity against HER2-negative MDA-MB-231 cells compared to NK cells alone. These results confirm that the individual components of SE-NK/T-DM1 cells are factors in producing the combinatorial anticancer efficacy. Moreover, embedding ADCs in immune cells using our one-step method enhances the anticancer efficacy beyond ADC alone, immune cells alone, or cotreatment of ADC and immune cells. To determine whether or not NK cells were activated upon incorporation of DMPE-PEG-T-DM1 on their surface, the level of CD107a expression, a prominent degranulation marker, on SE-NK/T-DM1 cells and unmodified NK cells was assessed upon engaging the target cancer cells. As a positive control, NK cells and SE-NK/T-DM1 cells were activated through PMA/Ionomycin stimulation. In NK cells and T-DM1+NK cell cotreatment groups, the levels of CD107a expression stayed at the basal level even when incubated with the cancer cells, Expression of CD107a was however amplified in SE-NK/T-DM1 cells upon contact with the target cancer cells, SK-BR-3 cells, and Calu-3 cells. This increase was absent in the nontarget MDA-MB-231 cells. These results suggest the absence of nonspecific activation of NK cells following the surface modification with DMPE-PEGT-DM1 and support the target-specific activation of SE-NK/T-DM1 cells. The in viva anticancer activity of SE-NK/T-DM1 cells was compared to that of T-DM1+1\1K cotreatment using HER2-positive Calu-3 models and HER2-negative MDA-MB-231 models. Tumor-bearing NOD scid Gamma (NSG, NOD.Cg-Prkdcscid Il2rgtm1WjI/SzJ) mice administered with $1 \times 10^7$ SE-NK/T-DM1 cells received ≈210 µg of T-DM1, which is similar to the recommended dose found in the literature for mice models (7-10 mg kg-1). In the HER2-positive tumor model, SE-NK/T-DM1 cells exhibited the strongest anticancer efficacy through the combinatorial effects (see FIG. 4A), The T-DM1+NK cotreatment inhibited tumor growth when compared to the control group. Treatment of SE-NK/T-DM1 cells demonstrated a substantial suppression in tumor growth compared to the T-DM1+NK cotreatment. In the HER2-negative tumor model, no significant difference in the tumor growth suppression was observed among all treatment groups (see FIG. 4B). The Calu-3 models and MDA-MB-231 models had steady body weights during the study period, indicating that the treatments caused no severe toxicity.

For the biodistribution of SE-NK/T-DM1 cells in Calu-3 tumor models, negligible accumulation of NK cells was observed in the heart, kidneys, and lungs (see FIG. 4C). While NK cells were detected in the liver and spleen, no significant differences in the number of NK cells were observed among the treatment groups, Compared to the unmodified NK cells and T-DM1+NK cotreatment, a greater number of NK cells were spotted in the tumor tissues that received SE-NK/T-DM1 cells. The in vivo experimental results from the efficacy and biodistribution studies confirm that SE-NK/T-DM1 cells prepared by our one-step method selectively migrate toward targeted tumor tissue and induce cancer cell death. Surface engineering of NK cells with T-DM1 enabled simultaneous accumulation of T-DM1 and NK cells in the target tumor tissue. Binding of T-DM1 to HER2-positive cancer cells would inhibit the downstream signaling pathway associated with P13K and AKT and the chemotherapeutic agent, DM1, disrupts the microtubule networks in the target cells, both of which lead to cell cycle arrest and cell apoptosis. SE-NK/T-DM1 cells migrated toward the antigen-expressing cancer cells from physical contact with the target cancer cells, which in turn increased the chance to stimulate the cytolytic function of NK cells. These NK cells in close contact with the target cancer cells, then, eradicate the cancer cell undergoing apoptosis by recognizing damage-associated molecular patterns (DAMP) expressed on the dying cancer cells. Allogeneic immune cells, the cell-of-interest to be weaponized by the one-step method herein, gained attention as a suitable solution to reinforce the diminishing active immune cell population in cancer patients due to their low occurrence adverse effects, high tumor-specific cytotoxicity, predictable anticancer activity, and ease of ex vivo expanding, maintaining, and activating a large cell population. Using the one-step method herein, advanced immune cells with a specific tumor-homing capability and potent anticancer activity based on chemoimmunotherapy can be generated instantly at the bedside, greatly reducing the time and cost required to obtain sufficient tumor-reactive immune cells. More importantly, the surface-engineered immune cells with ADCs generated herein would have enhanced efficacy even in solid tumors because antibodies, chemotherapeutic agents, and immune cells, all of which comprise our advanced immune cells, work in concert to eradicate the target cancer. One consideration with respect to expanding the application of hydrophobized ADCs to other immune cells may be the presence of Fc receptors. The conjugation of DMPE-PEGs to ADCs may circumvent the issue by masking the Fc region to increase the steric hindrance that lowers the binding affinity of Fc receptors on immune cells. Other creative antibody engineering methods, such as using single chain variable fragment (scFv) and altering Fc region to reduce Fc receptor binding affinity, can be employed as an alternative strategy for the surface engineering purpose.

Various modifications of the invention, in addition to those described herein, will be apparent to those skilled in the art from the foregoing description, Such modifications are also intended to fall within the scope of the appended claims. Each reference cited in the present application is incorporated herein by reference in its entirety. Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A chemoimmunotherapeutic composition for targeting a HER2 expressing cancer cell, said composition comprising:
    a) a targeting moiety specific for and capable of binding to a target on a cell of interest, wherein the targeting moiety is trastuzumab;
    b) a drug conjugated to the targeting moiety forming a targeting moiety-drug complex, wherein the drug is emtansine (DM1);
    c) a phospholipid linked to a polyethylene glycol (PEG) forming a phospholipid-PEG linker, wherein the phospholipid-PEG linker is attached to the targeting moiety-drug complex; and
    d) an immune cell, wherein the targeting moiety-drug complex is hydrophobically bound to the immune cell via the phospholipid-PEG linker, wherein the immune cell is a natural killer (NK) cell;
    wherein the targeting moiety-drug complex directs the immune cell to the cell of interest,
    wherein the drug has a cytotoxic effect on the cell of interest.

2. The composition of claim 1, wherein the phospholipid is selected from the group consisting of 1,2-dimyristoyl-sn-glycero-3-phosphoethanolamine, 1,2-dipalmitoyl-sn-glycero-3-phosphoethanolamine and 1,2-distearoyl-sn-glycero-3-phosphocholine.

3. The composition of claim 1, wherein the PEG has a molecular weight from 2 kDa to 10 kDa.

4. The composition of claim 1, wherein the cell of interest is a breast cancer cell.

5. A method of treating a HER2 expressing tumor in a subject in need thereof, comprising administering a chemoimmunotherapeutic composition comprising:
    a) a targeting moiety specific for and capable of binding to a target on a cell of interest wherein the targeting moiety is trastuzumab;
    b) a drug conjugated to the targeting moiety forming a targeting moiety-drug complex, wherein the drug is emtansine (DM1);
    c) a phospholipid linked to a polyethylene glycol (PEG) forming a phospholipid-PEG linker, wherein the phospholipid-PEG linker is attached to the targeting moiety-drug complex; and
    d) an immune cell, wherein the targeting moiety-drug complex is hydrophobically bound to the immune cell via the phospholipid-PEG linker, wherein the immune cell is a natural killer (NK) cell;
    wherein the targeting moiety-drug complex directs the immune cell to the cell of interest,
    wherein the drug has a cytotoxic effect on the cell of interest.

6. The method of claim 5, wherein the phospholipid is selected from the group consisting of 1,2-dimyristoyl-sn-glycero-3-phosphoethanolamine, 1,2-dipalmitoyl-sn-glycero-3-phosphoethanolamine and 1,2-distearoyl-sn-glycero-3-phosphocholine.

7. The method of claim 5, wherein the PEG has a molecular weight from 2 kDa to 10 kDa.

8. The method of claim 5, wherein the cell of interest is a breast cancer cell.

* * * * *